United States Patent [19]

Steele et al.

[11] Patent Number: 5,200,191

[45] Date of Patent: Apr. 6, 1993

[54] SOFTGEL MANUFACTURING PROCESS

[75] Inventors: Don Steele, Westlake; Gregory Dietel, Moorpark, both of Calif.

[73] Assignee: Banner Gelatin Products Corp., Chatsworth, Calif.

[21] Appl. No.: 757,553

[22] Filed: Sep. 11, 1991

[51] Int. Cl.$^5$ .............................................. A61K 9/48
[52] U.S. Cl. .................................... 424/453; 424/441; 424/456; 264/4.3; 264/4.4
[58] Field of Search .................. 264/4.4, 4.3; 424/463, 424/441, 456, 453

[56] References Cited

U.S. PATENT DOCUMENTS

| | | | |
|---|---|---|---|
| 4,067,960 | 1/1978 | Fadda | 424/455 |
| 4,166,800 | 9/1979 | Fong | 264/4.4 |
| 4,198,391 | 4/1980 | Grainger | 424/455 |
| 4,744,988 | 5/1988 | Brox | 424/456 |
| 4,780,316 | 10/1988 | Brox | 424/456 |
| 4,816,259 | 3/1989 | Matthews | 424/463 |
| 4,892,766 | 1/1990 | Jones | 424/456 |
| 4,935,243 | 6/1990 | Borkan | 424/441 |
| 5,023,024 | 6/1991 | Kyogoku | 264/4.3 |

OTHER PUBLICATIONS

P. Johns & A. Courts, The Science and Technology of Gelatin, "Relationship between Collagen and Gelatin", 1977.
Canadian Journal of Pharmaceutical Sciences, "The Mechanical Properties of Gelatin Films", vol. 13, No. 4 (1978).
Nature, "The Incipient Shrinkage of Collagen and Gelatin", vol. 159, p. 538 (Apr. 19, 1947).
Journal of Applied Polymer Science, "Creep Studies on Gelatin at 100% Relative Humidity", vol. IV, Issue No. 11, pp. 200–202 (1960).
P. Tyle, editor, Specialized Drug Delivery Systems, "Softgels: Manufacturing Considerations", Marcel Dekker, Inc., pp. 409–449 (1990).
Van Hostetler & J. Q. Bellard, The Theory and Practice of Industrial Pharmacy, "Capsules", pp. 346–383 (1970).
M. S. Patel, F. S. Morton and H. Seager, Manufacturing Chemists, "Advances in Softgel Formulation Technology", (Jul. 1989).
William R. Ebert, Pharmaceutical Technology, "Soft Elastic Gelatin Capsules: A Unique Dosage Form", Oct. 1977.
H. Seager, Pharmaceutical Technology, "Soft Gelatin Capsules: a solution to many tableting problems", Sep. 1985.
A. Veis, The Macromolecular Chemistry of Gelatin, "Physical Properties of Collagen Fibers", 1964.

Primary Examiner—Thurman K. Page
Assistant Examiner—William E. Benston, Jr.
Attorney, Agent, or Firm—Spensley Horn Jubas & Lubitz

[57] ABSTRACT

After softgels are encapsulated and dried in a drying tunnel, the resulting softgels are subjected to a further stress relieving step. During the stress relieving step, the temperature and humidity conditions in the drying tunnel are heightened. By utilizing the stress relieving step, the volume and number of dimples and bubbles in the softgels are reduced, and dimensional uniformity is maximized.

24 Claims, 3 Drawing Sheets

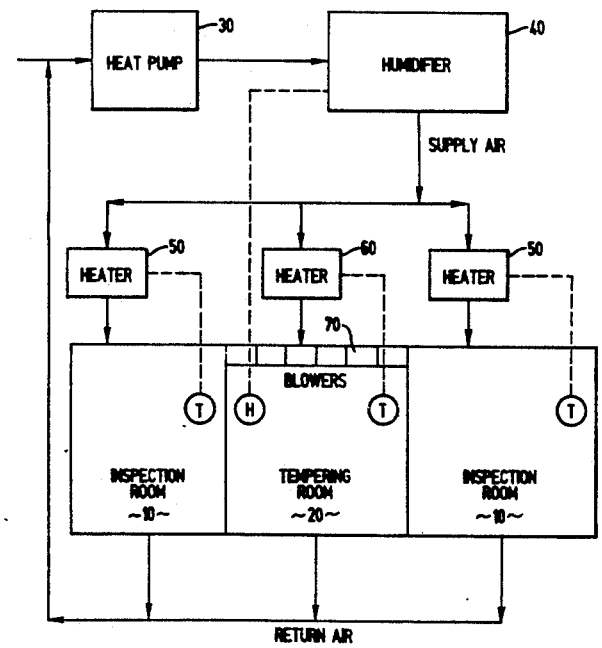

SOFTGEL MANUFACTURING PROCESS

1. FIELD OF THE INVENTION

This invention relates generally to the field of pharmaceutical manufacturing processes and specifically to the field of softgel manufacturing processes.

2. RELATED ART

The need for encapsulation of liquids, semi-solids, and pastes within a gelatin shell in such a way as to preclude uncontrolled leakage has resulted in the development of a very fundamental dosage form: the soft gelatin capsule. The first version was developed in the middle of the 19th century. While an arduous and not particularly accurate process initially, current manufacturing processes are fully automated, with a high degree of precision.

The softgel [the currently accepted nomenclature adopted by the SoftGel Association] is a one-piece, hermetically sealed soft gelatin shell containing a liquid, a suspension, or a semi-solid.

The most common modern manufacturing process involved in the preparation of softgels is a continuous method whereby two gelatin ribbons pass between twin rotating dies. As the ribbons meet, the liquid to be encapsulated is precisely injected between them. The capsule halves are sealed and ejected by the continuous rotation of the dies. See P. Tyle, *Specialized Drug Delivery Systems*, Marcel Dekker, Inc. (1990) for a general discussion of softgel manufacturing and production technology, in particular, Chapter 10 by Paul K. Wilkinson and Foo Song Hom.

Various gelatin shell masses may be prepared, depending on the fill properties, climatic conditions, and end use. Typically gelatin formulations include the same basic ingredients, namely, gelatin, a plasticizer such as glycerin, water, and optionally preservatives. The formulations of gelatins are well known to those of ordinary skill in the art.

In most cases, the typical rotary die process requires a flowable liquid or fill. The fill may be a single phase liquid active, a mixture of miscible liquids, or a solution or a suspension of solids and liquids. Generally the fill contains glycerin and a medicament. The liquids to be encapsulated in a gelatin shell are also well known to those of ordinary skill in the art.

Shell and fill formulations are discussed in Van Hostetler and J. Q. Bellard noted below as well as in "Advances in Softgel Formulation Technology", M. S. Patel, F. S. S. Morton and H. Seager, *Manufacturing Chemists*, July 1989; "Soft Elastic Gelatin Capsules: A Unique Dosage Form"; William R. Ebert, *Pharmaceutical Technology*, October 1977; "Soft gelatin capsules: a solution to many tableting problems", H. Seager, *Pharmaceutical Technology*, September 1985; U.S. Pat. No. 4,067,960 to Fadda; U.S. Pat. No. 4,198,391 to Grainger; U.S. Pat. No. 4,744,988 to Brox; and U.S. Pat. No. 4,780,316 to Brox. These references are incorporated herein by this reference.

After the rotary die process is used to thereby produce gelatin shells having a medicament fill therein, the resulting capsules are typically washed with an evaporatable solvent. Thereafter, the capsules are typically tumble dried in a series of hollow drums with perforated walls. Heated dry air is continuously pumped through the rotating drums at an air temperature typically less than 35° C. The warm air being blown into the capsules appears to penetrate the shell and cause it to dry from the inside by moving the water outward to the surface of the capsule. By the time the capsules exit this process, all of the solvent used in washing has typically been evaporated, and a large proportion (50–60%) of the water from the gelatin shell has been removed. Recent developments in drying include bypassing the drum drying stage and having the capsules dried in a drying tunnel or room as discussed below.

After the capsules exit the last drying drum, the capsules are typically spread on drying trays. The final drying phase for softgels is typically accomplished by passing the drying trays through drying tunnels or into drying rooms. Stacks of trays are inserted into drying tunnels or drying rooms, in which controlled temperature air (21°–24° C.) and low relative humidity (20–30%) is continuously circulated. Although additional water may be removed from dry capsules by further heating, for example at 40° C., such a procedure has not been found to be practical or necessary. See Van Hostetler and J. Q. Bellard in *The Theory and Practice of Industrial Pharmacy*, "Capsules", (1970), Chapter 13 at pages 346–383, and in particular at page 380.

The drying time, for most softgels, is 16–24 hours, but may be slightly longer if the softgels are over 20 minims in size or if the softgels contain a non-oily type liquid base.

Softgels permitted to come to water equilibrium in this controlled environment are considered "dry". The gelatin fill and shell of such "dry" softgels contain 6–10% water depending on the specific gelatin and fill formula used.

After drying, the capsules are typically inspected and finished using varied known techniques.

3. THE PROBLEMS AND OBJECTS OF THE INVENTION

Despite well known manufacturing processes for softgels, a number of significant problems exist. During the inspection step, it is quite common to find softgels having dimples in the shell and bubbles in the fill. The dimples and bubbles are unsightly in appearance and reduce the overall quality of the softgel batch. Thus those defective softgels must be rejected or thrown away. Consequently as a result of such dimples and bubbles, softgel production efficiency is decreased.

Moreover it is highly desired that the softgel manufacturing process result in a batch of dimensionally uniform softgels. Typically uniformity of a softgel is measured by the standard deviation in the lengthwise and widthwise measurement of an oblong softgel or the diameter of a round softgel. Although attempts have been made to produce more dimensionally uniform products, for example, products having a reduced dimensional standard deviation, softgels produced after typical drying processes often result in an unacceptable standard deviation.

It is therefore an object of the present invention to provide a softgel manufacturing process which results in softgel products having a minimal volume and number of dimples and bubbles, and which are relatively dimensionally uniform.

SUMMARY OF THE DISCLOSURE

The problems of dimples, bubbles and product dimensional uniformity have been greatly reduced by the present invention which is a significant advance in the art of softgel manufacturing processes. The inventors have discovered that by subjecting "dry" softgels to a subsequent stress relieving step, the volume and number of defects such as dimples and bubbles existing in the softgels prior to the stress relieving step can be substantially reduced. In addition, the stress relieving step reduces dimensional standard deviation thereby resulting in more dimensionally uniform batches of softgels.

The stress relieving step comprises subjecting the "dry" capsules to a subsequent heating step at a heightened temperature and relative humidity. By subjecting the "dry" softgels to this step, dimples and bubbles are removed from the softgels and the dimensional standard deviation is preferably reduced.

BRIEF DESCRIPTION OF THE DRAWINGS FIGURES

FIG. 1 is a schematic showing the stress relieving or tempering room.

FIGS. 2A and B are before and after photographs of softgels subjected to the stress relieving step.

DETAILED DESCRIPTION OF THE PREFERRED EMBODIMENTS

Figure 1:
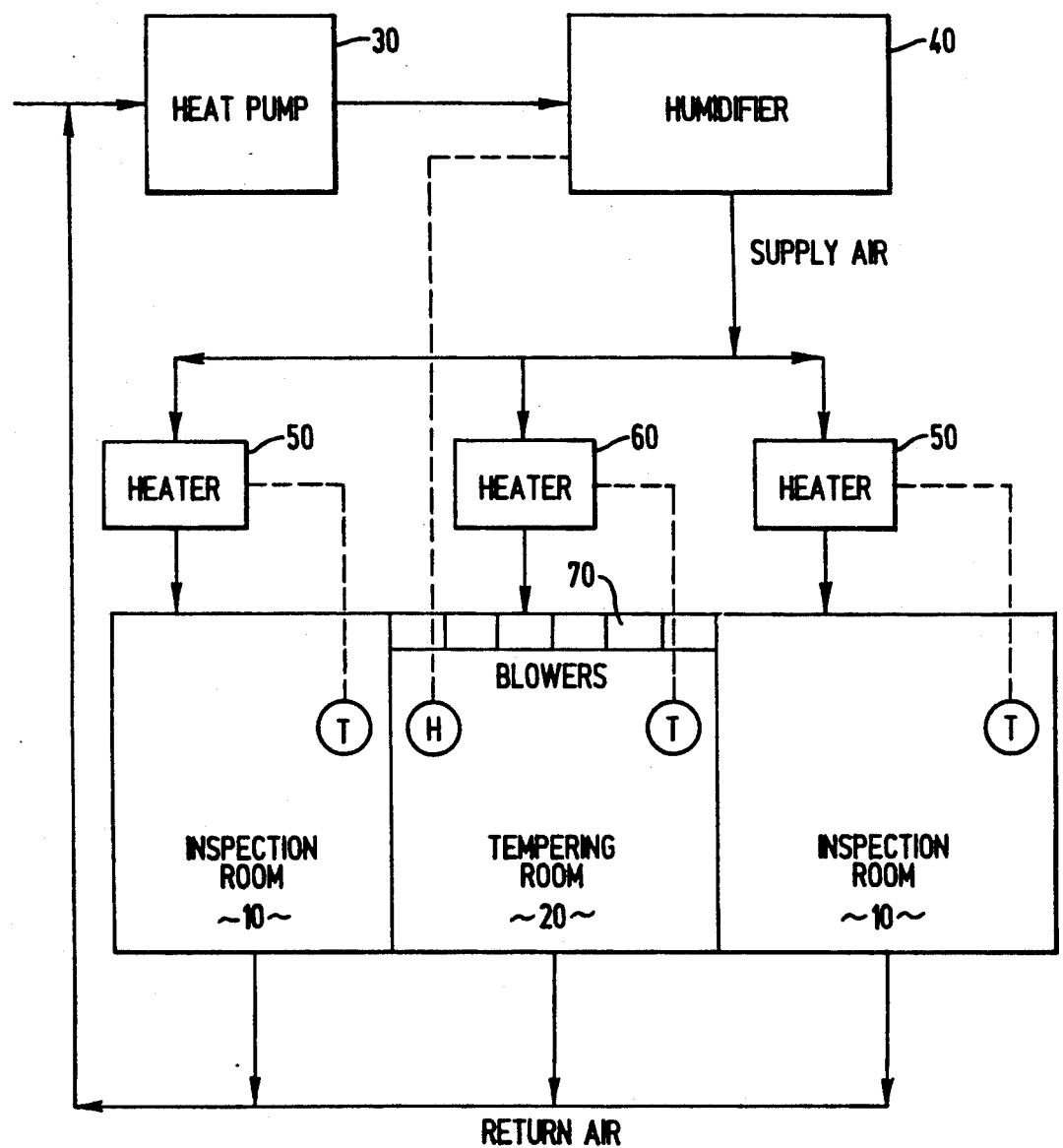

Softgels are generally prepared by encapsulating a medicated fill in a gelatin shell. The shells and fills are prepared according to formulations well known to those of skill in the art. For example, a typical gelatin shell formulation might include (by weight):

| | |
|---|---|
| Gelatin | 47% |
| Glycerin, USP | 15% |
| Water | 38% |
| 30 Colors | |

The shell can be filled by standard encapsulation techniques with a variety of fills including PEG and propylene glycol.

A typical hygroscopic medicated fill might include (by weight):

| ACTIVES: | Acetaminophen (APAP) (250 mg) | 27% |
|---|---|---|
| | Pseudoephedrin HCl (30 mg) | 3% |
| | Dextromethorphan HBr (15 mg) | 1.6% |
| | Doxylamine Succinate (6.25 mg) | .6% |
| INACTIVE: | Polyethylene Glycol (PEG) | 67.8% |

Although the example above uses a hydrophilic fill, other fills are within the scope of the present invention. In addition, the PEG can be PEG 400 or a PEG of higher molecular weight. Further, the use of sorbitol free shells appears to facilitate the stress relieving step.

The softgels can be encapsulated using known fills and shells by techniques known to those of skill in the art, for example, either the plate method or the continuous rotating die methods described previously.

After the encapsulation and washing steps, the resulting capsules are typically dried in drying tunnels or rooms for about 3-7 days to remove water in the hygroscopic fill and the shell to about 6-10% by volume. These are typically called "dry" capsules. The Karl Fischer test is used for determining water content. The drying occurs typically at about 21°-24° C. and at a relative humidity of 20-40%. One can use infrared radiation to dry out the water as an alternative.

The amount of time the capsules are in the drying tunnels or room depends on the thickness of the gelatin shell, the amount of oil on the surface of the gel after the washing step, the density of capsules on the trays, and other factors known to those of ordinary skill in the art.

After the capsules are "dry", they are subjected to the novel step of the present invention, namely a stress relieving step.

The stress relieving step is also referred to herein as a subsequent heating step or a tempering step. In general, the stress relieving step involves a change in the conditions of temperature and relative humidity from the drying step. By changing the conditions of temperature and relative humidity, dimples in the shell and bubbles in the fill are substantially removed. In addition, the product preferably becomes more dimensionally uniform.

The stress relieving step can take place in the same tunnel's or drying rooms or tempering rooms as the prior drying step, and thus no new equipment or additional labor is required. Moreover, the stress relieving step can be accomplished in the continuum of the drying step. For example, capsules could be dried for three days in drying tunnels and subsequently stress relieved with elevated temperature and humidity conditions. In such case, the bubbles and dimples would not be observed. This is due to the fact that drying continues during the time period that the product is in the tempering room.

With reference to FIG. 1, there is shown in block layout form an illustrative and preferred air conditioning system for inspection rooms 10 and a tempering room 20 which can selectively maintain 21°-43° C. and 35-60% relative humidity. The tempering room can be used for the drying and stress relieving steps.

As can be seen from the block layout there is one 7½ ton heat pump 30 with a second unit (not shown) as a back up, a humidifier 40, two 10 KW duct strip heaters 50, and one 15 KW duct heater 60 for supplying air to each room. Also the tempering room 20 has six 3000 CFM blower fans 70 mounted at one end of the tempering room for circulating room air and a filter bank exhaust (not shown) at the opposite end of the room. Each room is also supplied with a temperature thermostat (not shown) that controls the duct strip heaters. There is a humidistat (not shown) mounted in the tempering room which controls the humidifier 40.

Figure 2A:
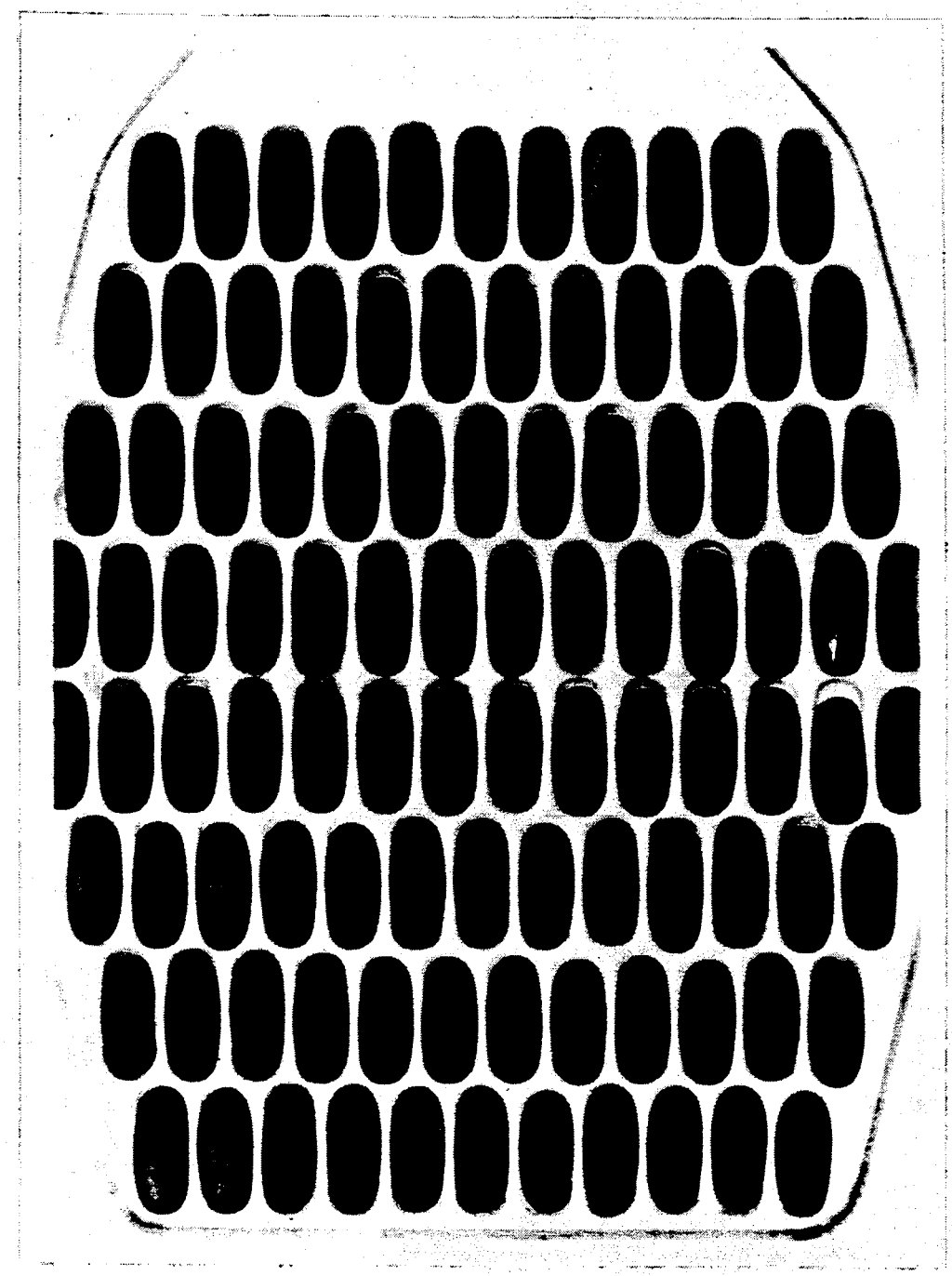

The degree to which defects such as dimples and bubbles are removed can be measured by considering the number and volume of dimples and bubbles prior to the stress relieving step as compared to the number and volume following the stress relieving step. FIGS. 2A and B are photographs of a batch of softgels before the stress relieving or tempering step and thereafter.

The softgel capsules shown had the following formulation (by weight):

| Shell: | Gelatin | 47% | |
|---|---|---|---|
| | Glycerin | 15% | |
| | Water | 38% | (plus coloring agent and before drying step) |
| Fill: | Polyethylene Glycol | 100% | (920 mg) |

One hundred capsules were placed on a counting tray after being measured individually. These capsules were previously dried for nine days to a water content of 7.9% under conditions of 27% relative humidity and 24° C. to thereby constitute "dry" softgels.

Figure 2B:
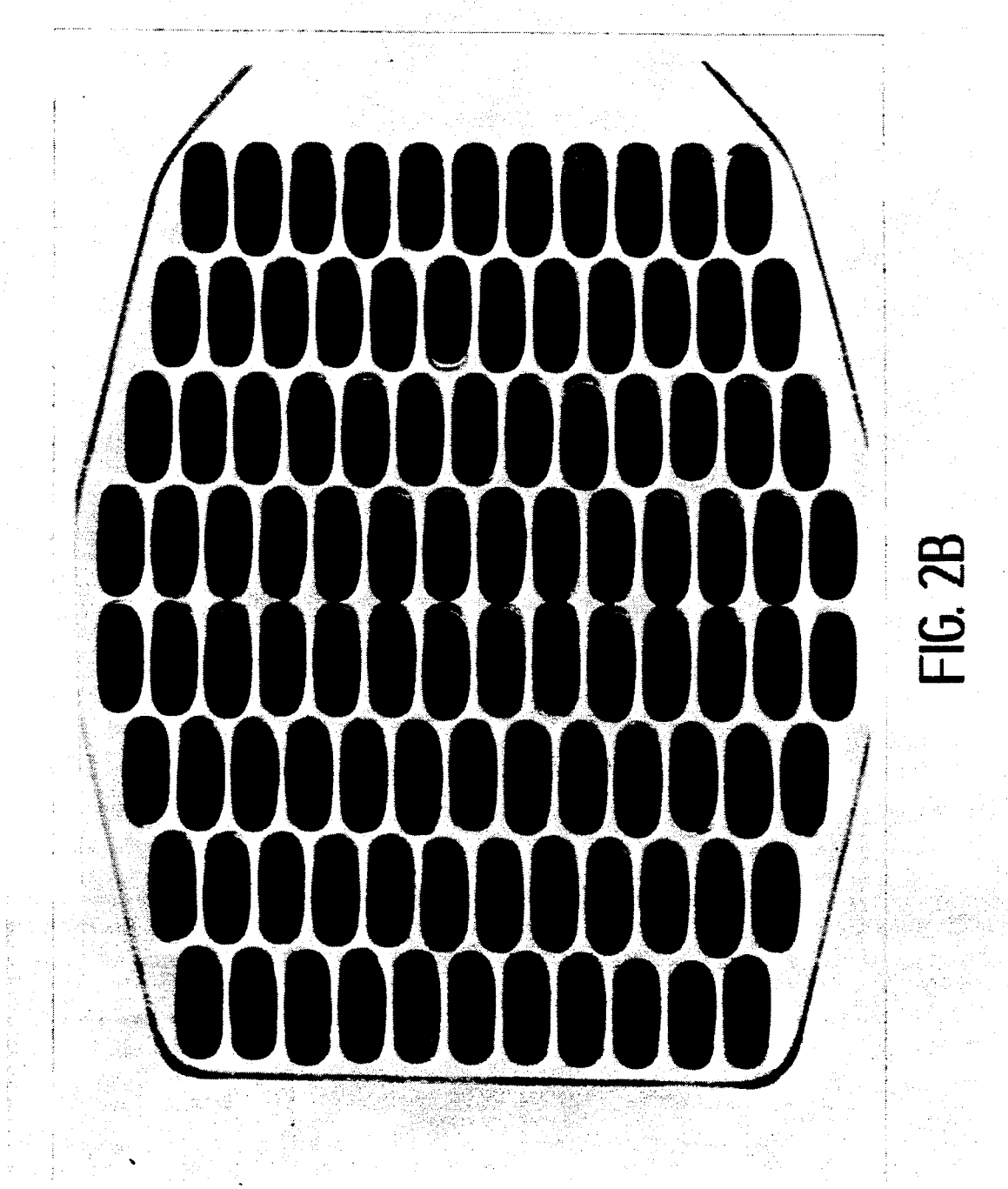

As indicated by the before photograph in FIG. 2A, all of the capsules contained bubbles. These capsules were stress relieved at 35° C. and 45% relative humidity for 20 hours, and then re-photographed as shown in FIG. 2B. As can be seen, all bubbles with the exception of two were eliminated and the dimensional variation of the capsules was reduced. That is, the standard deviation of the length was reduced from 0.00458 to 0.00428 inches and of the width from 0.00360 to 0.00336 inches.

These same capsules were returned to the tempering room for an additional 20 hours. After the second tempering, no bubbles remained.

The present invention is intended to decrease the volume of dimples and bubbles by at least 25%, preferably by 50%, more preferably by at least 75%, and optimally by 95-100%. The decrease in dimples and bubbles can readily be visually seen during inspection of the softgels before and after the stress relieving step.

Generally, the stress relieving step is accomplished at a temperature within the preferred range of 32° and 38° C. It is possible to stress relieve the capsules at a temperature above 43° C. depending upon the fill and gelatin formula. The temperature should not be so high such that the capsules would melt. 43° C. is generally at the high end, although preferably the high end is 38° C.

On the other hand, the temperature range at the low end is preferably about 35° C. If the temperature is much lower than 35° C., the stress relieving may not be adequate or else the stress relieving step may take an undesirable and impractical length of time.

Thus, in general, it is preferable that the temperature of the drying tunnels or drying rooms during the stress relieving step range from 32° to 43° C., and more preferably from 35° to 38° C.

During the stress relieving step, it is also important that the relative humidity within the tunnels or tempering room range from about 35% to about 60%, preferably 35-45%, and optimally 40-45%. Employing this relative humidity range, coupled with the heightened temperature, unexpectedly provides to softgel batches the long needed increase in topographical and dimensional uniformity.

The humidity range is meant to match the equilibrium relative humidity (ERH) of the capsules. If the tunnel or tempering room relative humidity is below 35%, excessive drying may occur. If the relative humidity is above 60%, water may be added to the gelatin and fill resulting in a poor product.

From a general standpoint, the stress relieving step will be at that temperature, relative humidity and for that time period that will remove substantially all dimples and bubbles, and preferably that will minimize dimensional standard deviation.

Generally, the stress relieving step will take at least one hour, preferably at least two hours. The general range is about 1 to 75 hours, although over 75 hours is within the scope of the present invention.

The process of the present invention is also characterized by improving the consistency or uniformity of the softgels and reducing the standard deviation of the softgel dimensions. When comparing the standard deviation of the softgel dimensions (length and width) prior to the stress relieving step and after the stress relieving step, it is preferred that the standard deviation decrease by at least 5%, and more preferably by 5-10%.

For example, the standard deviation of the length of 100 softgels according to the APAP formula set forth above and before the stress relieving step was 0.0045 inches. Practicing the stress relieving step on 100 capsules of the formulation referred to above in the temperature range of 35°-38° C., at a relative humidity of 35-45%, and for 20 hours, resulted in the standard deviation being reduced to 0.0042 inches, representing a 7.4% reduction.

After the stress relieving step, the softgels are typically brought to room temperature and preferably kept at a relative humidity of about 35-45% in the packaging operation. Thereafter, the softgels are placed into bottles or blister packs or another fairly airtight system at a relative humidity of about 30-45%.

The present invention reduces defects such as dimples and bubbles, provides a more uniform product which facilitates subsequent operations such as printing and blister packaging, and improves shelf life stability resulting from the stress caused by water loss during drying, gelatin shrinkage and material migration.

It will thus be seen that the objects set forth above, and those made apparent from the preceding description, are efficiently attained. Since certain changes may be made without departing from the scope of the invention, it is intended that all matter contained in the above description shall be interpreted as illustrative and not in a limiting sense.

Alternative methods of heating the capsules may be used to stress relieve the capsules resulting in shortened processing times. Examples are microwave, ultrasound and infrared radiation.

In addition, the present invention is not limited to softgels, but may be used in connection with other substances having bubbles or dimples where such substances are at least breathable and preferably diffusible by water.

We claim:

1. In a process for producing a plurality of gelatin shells encapsulating a fill, wherein the fill is first encapsulated in a shell and then the shells containing the fill are dried at a given temperature so that the water content of each shell ranges from 6–10%, the improvement comprising subsequently heating the filled shells to a temperature above the given temperature and in a range of 32°–43° C. and at 35–60% relative humidity whereby dimples and bubbles are removed from the filled shells.

2. The process according to claim 1 wherein the heating is accomplished at a temperature range of 35°–38° C.

3. The process according to claim 1 wherein there are a plurality of oblong filled shells, the oblong shells having a length and a width, and wherein the standard deviation of the filled shell lengths and widths after the subsequent heating step has decreased.

4. The process according to claim 3 wherein the standard deviation has decreased by at least 5%.

5. The process according to claim 1 wherein the filled shells are softgels and the fill is hygroscopic.

6. The process according to claim 1 wherein the subsequent heating step occurs for a time period sufficient to remove substantially all dimples and bubbles.

7. The process according to claim 6 wherein the time period is at least 1 hour.

8. The process according to claim 7 wherein the time period ranges from 1 to 75 hours.

9. The process according to claim 8 wherein the time period is about 2 hours.

10. The process according to claim 6 wherein over 95% of bubbles and dimples existing prior to the stress relieving step are removed.

11. The process according to claim 1 wherein the shells are one-piece, hermetically sealed soft gelatin shells.

12. A process for producing softgels, the process comprising the following steps: encapsulating a fill in a shell to form filled capsules; drying the resulting capsules; and thereafter stress relieving the resulting capsules by heating the capsules at a temperature and relative humidity greater than the temperature and relative humidity used to dry the capsules and for a time period sufficient to remove substantially all dimples and bubbles.

13. The process according to claim 12 wherein the drying step occurs at a relative humidity of 20-40% and the stress relieving step occurs at a relative humidity of 35-60%.

14. The process according to claim 13 wherein the drying step occurs within a temperature range of 21°-24° C. and the stress relieving step occurs within a temperature range of 32°-43° C.

15. The process according to claim 14 wherein the stress relieving step occurs at a temperature within the range of 35°-38° C.

16. The process according to claim 12 wherein there are a plurality of filled shells and the standard deviation of the filled shell lengths and widths after the stress relieving step has decreased by at least 5%.

17. The process according to claim 16 wherein the fill is hygroscopic and the drying and stress relieving step result in capsules having 6-10% by volume water in the shell.

18. The process according to claim 17 wherein the shell is sorbitol free.

19. The process according to claim 12 wherein the stress relieving step occurs for a time period sufficient to remove substantially all dimples, and bubbles.

20. The process according to claim 19 wherein the time period ranges from 1 to 75 hours.

21. The process according to claim 20 wherein the time period is at least about 2 hours.

22. A process for improving topographical and dimensional uniformity of softgels, the process comprising, after initiation of drying of the softgels, heating the softgels at a temperature and relative humidity greater than the temperature and relative humidity used to initially dry the softgels and for a time period sufficient to remove substantially all dimples and bubbles.

23. The process of claim 22 wherein after initiation of drying of the softgels the temperature and relative humidity are increased such that the temperature is above 32° C. and the relative humidity is above 35%.

24. The process of claim 22 wherein the volume of bubbles and dimples in the softgels has decreased by at least 25% when comparing the volume before and after the softgels are subjected to the increased temperature and humidity.

* * * * *